US012766222B2

(12) United States Patent
Hwang et al.

(10) Patent No.: US 12,766,222 B2
(45) Date of Patent: Oct. 20, 2026

(54) COMPOSITE FOR CONTROLLING DEGRADATION OF TRANSIENT ELECTRONICS

(71) Applicant: ANPOLY, Pohang-si (KR)

(72) Inventors: Dong Soo Hwang, Pohang-si (KR); Tae Il Kim, Pyeongtaek-si (KR); Hyung Joon Cha, Pohang-si (KR)

(73) Assignee: ANPOLY, Pohang-si (KR)

( * ) Notice: Subject to any disclaimer, the term of this patent is extended or adjusted under 35 U.S.C. 154(b) by 452 days.

(21) Appl. No.: 18/262,004

(22) PCT Filed: Nov. 25, 2021

(86) PCT No.: PCT/KR2021/017493
§ 371 (c)(1),
(2) Date: Jul. 18, 2023

(87) PCT Pub. No.: WO2022/203157
PCT Pub. Date: Sep. 29, 2022

(65) Prior Publication Data

US 2024/0299623 A1 Sep. 12, 2024

(30) Foreign Application Priority Data

Mar. 24, 2021 (KR) ........................ 10-2021-0038000

(51) Int. Cl.
*A61L 27/28* (2006.01)
*A61L 27/56* (2006.01)
*A61L 27/58* (2006.01)

(52) U.S. Cl.
CPC ............... *A61L 27/28* (2013.01); *A61L 27/56* (2013.01); *A61L 27/58* (2013.01); *A61L 2300/604* (2013.01); *A61L 2400/18* (2013.01)

(58) Field of Classification Search
CPC .......... A61B 2562/0261; A61B 5/4851; A61B 5/6846; A61L 2300/604; A61L 2400/18;
(Continued)

(56) References Cited

U.S. PATENT DOCUMENTS

| | | | |
|---|---|---|---|
| 2009/0317478 | A1 | 12/2009 | Han et al. |
| 2018/0230318 | A1 | 8/2018 | Lynn et al. |
| 2020/0276365 | A1 | 9/2020 | Nguyen et al. |

FOREIGN PATENT DOCUMENTS

| | | |
|---|---|---|
| CN | 101549176 A | 10/2009 |
| CN | 102224334 A * | 10/2011 |

(Continued)

OTHER PUBLICATIONS

International Search Report for PCT/KR2021/017493 by Korean Intellectual Property Office dated Mar. 10, 2022.

(Continued)

*Primary Examiner* — Lawrence D Ferguson
(74) *Attorney, Agent, or Firm* — BROADVIEW IP LAW, PC

(57) ABSTRACT

The present invention provides a composite for controlling the degradation of transient electronics, wherein the composite can control the degradation time of transient electronics, which are absorbed in the body and degrade after a predetermined time elapses, and thus can greatly improve the utility of the transient electronics. Moreover, the composite can degrade in the body through biodegradation, and has excellent flexibility and biocompatibility, and thus has sufficient biological stability and biocompatibility.

11 Claims, 8 Drawing Sheets

(58) Field of Classification Search
CPC .......... A61L 27/28; A61L 27/56; A61L 27/58; A61L 31/148; A61L 31/146
See application file for complete search history.

(56) References Cited

FOREIGN PATENT DOCUMENTS

| | | | |
|---|---|---|---|
| KR | 10-2013-0057983 | A | 6/2013 |
| KR | 10-2015-0096907 | A | 8/2015 |
| KR | 10-2016-0105172 | A | 9/2016 |
| TW | 201119652 | A1 | 6/2011 |
| WO | 2014/113382 | A1 | 7/2014 |

OTHER PUBLICATIONS

Bazaka, Kateryna et al. (2014). "Polymer encapsulation of magnesium to control biodegradability and biocompatibility". Journal of nanoscience and nanotechnology, 14(10), 8087-8093. DOI:10.1166/jnn.2014.9409.
Phan, Hoang-Phuong (2021). "Implanted Flexible Electronics: Set Device Lifetime with Smart Nanomaterials". Micromachines, 12(2), 157. DOI:10.3390/mi12020157.
Office Action for KR 10-2021-0038000 by Korean Intellectual Property Office dated May 31, 2025.
Office Action for CN 202180093445.7 by China National Intellectual Property Administration dated Mar. 28, 2026.

* cited by examiner

COMPOSITE FOR CONTROLLING DEGRADATION OF TRANSIENT ELECTRONICS

CROSS-REFERENCE TO RELATED APPLICATIONS

This application is a National Phase Entry Application of PCT Application No. PCT/KR2021/017493, filed on Nov. 25, 2021, which claims priority to Korean Patent Application No. 10-2021-0038000, filed on Mar. 24, 2021, in Korean Intellectual Property Office, the entire contents of which are hereby incorporated by reference in its entirety.

TECHNICAL FIELD

The present invention relates to a biodegradable composite for controlling the degradation of transient electronics.

BACKGROUND ART

With the advent of the era of the 4th Industrial Revolution and the development of the IoT technology, the demand for personalized medical technology in diagnosis and treatment through individualized health monitoring has been increasing, and the development of personalized high-tech medical devices is rapidly taking place. Biomedical transient electronics, an emerging next-generation technology, is in the spotlight as it uses bio-insertable medical devices that are absorbed into the body through biodegradation to carry out a specific diagnostic test or treatment directly.

Despite the advantages, however, the practical use of transient electronics has been limited for the following reasons.

First, since the transient electronics are degraded after a predetermined time elapses—from the time when they are injected into the living body till the specific function is carried out—the degradation time must be set differently according to the purpose for which the transient electronics are used. However, there is a problem in conventional technology when the degradation time cannot be controlled, particularly when they are absorbed in the body and are degraded either too quickly or too slowly. When introduced in the body to release a drug, there have been problems of not being able to control the time cycle of the drug release, or when they are attached to a specific organ, there is not sufficient time to perform various diagnostic tests.

Second, the transient electronics must not remain as a foreign substance after biodegradation in vivo but have enough flexibility and adhesion to be compatible with the surrounding tissue. However, due to the inability to control the degradation time in conventional technology, there have been reports of side effects including damage to organs from the transient electronics that remain in the body that are not completely compatible with uncontrolled flexibility and cell-adhesion.

Third, the transient electronics must not cause any immune response, side effect or cytotoxicity to surrounding cells once injected in vivo, but its sufficient immunological stability as biomedical device has not yet been reported.

Accordingly, there is a need for research on transient electronics that are capable of controlling the degradation time of transient electronics that are absorbed in vivo and degraded after a predetermined time elapses, thereby greatly improving the utility thereof, and at the same time, the transient electronics can be degraded in vivo through biodegradation and have excellent flexibility and biocompatibility such that they can sufficiently guarantee biological stability and biocompatibility.

RELATED ART DOCUMENTS

Patent Documents (Patent Document 0001) Korean Patent Publication No. 10-2015-0096907 (Aug. 26, 2015)

DISCLOSURE

Technical Problem

The present invention has been designed to overcome the aforementioned problems, and the first problem to be solved by the present invention is to control the degradation time of transient electronics that are absorbed in vivo and degraded after a predetermined time elapses, thereby greatly improving the utility thereof.

In addition, the second problem to be solved by the present invention is to exhibit flexibility and adhesion to the extent that it does not damage organs and the like by acting as a foreign substance in vivo such that it is possible to guarantee sufficient stability and biocompatibility to the extent that it does not cause immune responses or side effects in surrounding tissues even after transplantation into the body.

Technical Solution

In order to solve the aforementioned problems, the present invention provides a composite for controlling the degradation of transient electronics, which is a composite for controlling the degradation for degrading transient electronics that are degraded by a biological fluid at a desired time point, including a support; transient electronics that are formed on the support; and a degradation control unit for controlling the degradation time point of the transient electronics by sealing the transient electronics from a biological fluid with a porous polymer layer in which biocompatible oil is supported in internal pores.

In addition, according to an exemplary embodiment of the present invention, as time elapses after being in contact with the biological fluid, the biocompatible oil which is supported on the porous polymer layer of the composite for controlling the degradation of transient electronics flows out toward the biological fluid, and as a result, the biological fluid flowing into empty pores of the porous polymer layer eventually comes into contact with the transient electronics to degrade the transient electronics.

In addition, the support and the porous polymer layer may include at least one selected from the group consisting of polycaprolactone (PCL), polydioxanone (PDO), poly(L-lactide) (PLLA), poly(DL-lactide-co-glycolide) (PLGA), polyethylene oxide (PEO), polylactic acid (PLA) and polyvinyl alcohol (PVA), and the porous polymer layer may be formed of a polymer which is soluble in the biological fluid in order to control the degradation time point of the transient electronics together with the biocompatible oil.

In addition, the transient electronics may have a thickness of 10 to 1,000 nm.

In addition, the transient electronics may include at least one of a water-soluble conductive transient organic material or a water-soluble conductive transient inorganic material.

In addition, the degradation control unit may have an elongation of 60% or more.

In addition, the porous polymer layer may include internal pores having varied sizes.

In addition, the porosity of the porous polymer layer may be 10 to 90%.

In addition, the porous polymer layer may be composed of a first part and a second part that face a first surface on the first surface which is in contact with transient electronics and have different pore structures in the direction of a second surface which is in contact with the biological fluid.

In addition, at least one of the first part and the second part may have a fingerlike shape.

In addition, the window diameter of a surface on the side of the first surface and the window diameter of a surface on the side of the second surface may be different from each other.

In addition, the biocompatible oil may be any one or more hydrophobic biocompatible oils selected from the group consisting of fluorine-based oil, silicone-based oil, mineral oil and vegetable oil.

In addition, the present invention provides a medical device, including any one of the above-described composites for controlling the degradation of transient electronics.

Advantageous Effects

According to the present invention, since it is possible to control the degradation time of transient electronics that are absorbed in vivo and degraded after a predetermined time elapses, the utility thereof can be greatly improved. In addition, since it has flexibility and adhesion enough not to damage organs by acting as a foreign substance in the body, it can guarantee sufficient stability and biocompatibility such that it does not cause immune responses or side effects in surrounding tissues even after transplantation into the body.

MODES OF THE INVENTION

Figure 1:
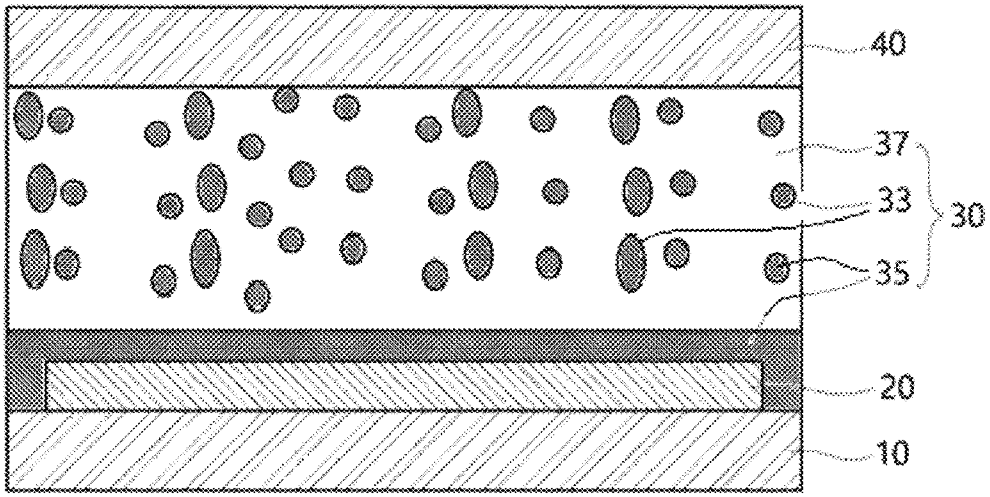
FIG. 1 is a cross-sectional diagram of the composite for controlling the degradation of transient electronics according to an exemplary embodiment of the present invention.

Hereinafter, the exemplary embodiments of the present invention will be described in detail so that those of ordinary skill in the art to which the present invention pertains can easily practice the present invention. The present invention may be embodied in many different forms and is not limited to the exemplary embodiments described herein.

As described above, the transient electronics that are degraded after a predetermined time elapses in vivo according to the related art cannot control the degradation time, lack flexibility and adhesion, or cause side effects such as immune responses, and thus, there has been great difficulty in using the same appropriately for the intended purpose.

Accordingly, the present invention has sought to solve the above-described problems by providing a composite for controlling the degradation of transient electronics, which is a composite for controlling the degradation for controlling the degradation time of transient electronics that are degraded by a biological fluid, including a support; transient electronics that are formed on the support; and a degradation control unit for controlling the degradation time of the transient electronics by sealing the transient electronics with a porous polymer layer in which biocompatible oil is supported in internal pores.

Through this, it is possible to control the degradation time of transient electronics introduced into the living body, thereby greatly improving the utility thereof, and since they act as a foreign substance in vivo, they have flexibility, biocompatibility and adhesion to the extent that they do not damage the organs and the like or cause immune responses or side effects even after transplantation into the body, thereby greatly improving biostability.

Hereinafter, the present invention will be described in detail with reference to FIGS. 1 to 10.

The present invention is a composite 100 for controlling the degradation for degrading transient electronics that are degraded by a biological fluid at a desired time point and includes a support 10.

The support 10 serves to physically support the transient electronics 20. In addition, the support 10 can be decomposed so as not to ultimately remain in vivo, and it is possible to additionally control the degradation time of transient electronics by adjusting the decomposition rate of the support.

To this end, the support 10 may include a biodegradable material that can be degraded in vivo without inducing an immune response in vivo as long as it meets the objects of the present invention. As non-limiting examples thereof, the biodegradable material may be a natural biodegradable polymer or a synthetic biodegradable polymer. As the natural biodegradable polymer, collagen, hyaluronic acid, chitosan, gelatin, alginic acid and the like may be used, and as the synthetic biodegradable polymer, it may include at least one selected from the group consisting of polycaprolactone (PCL), polydioxanone (PDO), poly(L-lactide) (PLLA), poly(DL-lactide-co-glycolide) (PLGA), polyethylene oxide (PEO), polylactic acid (PLA) and polyvinyl alcohol (PVA), Meanwhile, since the support 10 can be set to an appropriate thickness in consideration of the use for which the composite 100 for controlling the degradation of transient electronics according to the present invention is used, the need for additional control of the degradation time of transient electronics and the like, the thickness of the support 10 is not particularly limited, but may have a thickness of 10 to 400 nm, for example.

In addition, the support 10 may be implemented in a known conventional shape having flexibility and biocompatibility in vivo so as to be attached to an organ and the like, for example, in the form of a film as shown in FIG. 5.

Next, the composite 100 for controlling the degradation according to the present invention includes transient electronics 20 that are formed on the support 10.

The transient electronics 20 are injected into the living body to release a drug, or to be attached to a specific organ to perform various tests/diagnosis and the like to perform a function of diagnosis or treatment in vivo, and through the control of the degradation control unit 30, they can be biodegraded and absorbed into the body. However, the use of the transient electronics 20 is not limited to test/diagnosis or treatment, and it can be used for various functions and uses that can be degraded and absorbed in the living body after a predetermined time elapses.

In this case, according to a preferred exemplary embodiment of the present invention, when the transient electronics 20 are attached to a specific organ to perform various tests/diagnosis, the transient electronics 20 may be implemented by inorganic conductive transient electronics 20 or organic conductive transient electronics 20 that have conductivity, and particularly, since the transient electronics 20 must have flexibility enough not to damage organs and the like by acting as a foreign substance in vivo and must be sufficiently compatible with surrounding tissues even after transplantation in the body, they may be implemented as water-soluble organic conductive transient electronics 20 or water-soluble inorganic conductive transient electronics 20, and as long as they meet the objects of the present invention, they may be implemented by including a conventional biodegradable material.

In this case, since an appropriate thickness can be set according to the purpose for which the composite 100 for controlling the degradation of transient electronics according to the present invention is used, the thickness of the transient electronics 20 is not particularly limited, but according to a preferred exemplary embodiment of the present invention, when it is injected into the living body, it may have a thickness of 10 to 1,000 nm.

Next, the composite 100 for controlling the degradation according to the present invention includes a degradation control unit 30 which protects the transient electronics 20 from the outside until the transient electronics 20 are degraded and controls the degradation time point such that the transient electronics 20 are degraded after a certain time point.

The degradation control unit 30 includes a porous polymer layer 37 and a biocompatible oil 35 which is supported in the internal pores 33 of the porous polymer layer 37 as illustrated in FIG. 1, and after sealing the transient electronics 20, the biocompatible oil 35 which is supported in the internal pores 33 flows out to one surface which is in contact with the transient electronics 20 to cover the transient electronics 20, and through this, it is possible to protect the transient electronics 20 from an external environment including various biological fluids 40 such as blood, fluid, mucus and urine in the body.

In addition, the degradation control unit 30 serves to control the degradation time of the transient electronics 20.

In general, since the transient electronics are introduced into the living body to perform a specific function and are degraded after a predetermined time has elapsed, the degradation time of the transient electronics must be set to suit the purpose for which the transient electronics are used. However, according to the related art, there is a problem in that the degradation time of the transient electronics cannot be controlled, such as when the transient electronics introduced into the living body and degraded too quickly or too slowly. Accordingly, the transient electronics must be introduced into the living body to release a drug, but when the time and cycle of drug release cannot be controlled or when they are attached to a specific organ to perform various tests/diagnostics, there has been a problem in that the degradation time cannot be controlled to suit the purpose, such as not being able to guarantee a sufficient time.

Furthermore, there have been studies to control the degradation time of such transient electronics, but when a hydrophilic protective film layer is used, the transient electronics are degraded in response to a biological fluid within one day and cannot perform its intended function. Conversely, when a hydrophobic protective layer is utilized for the transient electronics, there has been a problem in that they have characteristics of both ends depending on the material of the transient electronics, such as a phenomenon that the transient electronics do not melt at all in the body.

Accordingly, in the present invention, the biocompatible oil 35 which is supported in the internal pores 33 of the porous polymer layer 37 is discharged to the outside over time, and forms an empty space in the internal pores 33 of the porous polymer layer 37, and the biological fluid 40 penetrates into the empty space to control the degradation time of the transient electronics 20. That is, after the degradation control unit 30 according to the present invention seals the transient electronics 20 and performs a desired function through the transient electronics 20, the amount of biocompatible oil 35 which is supported in the internal pores 33 of the porous polymer layer 37 of the degradation control unit 30 meets the biological fluid 40 and is discharged to the outside over time to be reduced, and the biological fluid 40 penetrates into the transient electronics 20 through the pores 33 supported by the oil 35. In this case, the permeated hydrophilic biological fluid 40 degrades the water-soluble transient electronics 20 over time. Accordingly, the biocompatible oil 35 may be a hydrophobic biocompatible oil that is insoluble in the biological fluid 40, and as non-limiting examples thereof, it may be any one or more hydrophobic biocompatible oils selected from the group consisting of fluorine-based oil, silicone-based oil, mineral oil and vegetable oil.

Meanwhile, the transient electronics must not only decompose themselves and remain as a foreign substance after a certain period of time has elapsed, but also have flexibility and adhesion to the extent that they do not damage organs and the like by acting as a foreign substance in the living body. However, according to the related art, there is a problem in that the flexibility and adhesion of the transient electronics cannot be controlled, and thus, they cannot be fully integrated in the living body, such as damage to organs and the like.

Accordingly, the degradation control unit 30 according to the present invention is introduced into the body and is flexibly attached to the inside of the living body without damage to organs and the like, and thus, it has an elongation at a certain level or more such that it can perform a function for a predetermined time. Such elongation may be controlled and adjusted through the pores 33 and the biocompatible oil 35 of the porous polymer layer 37 constituting the degradation control unit 30.

Figure 2A:
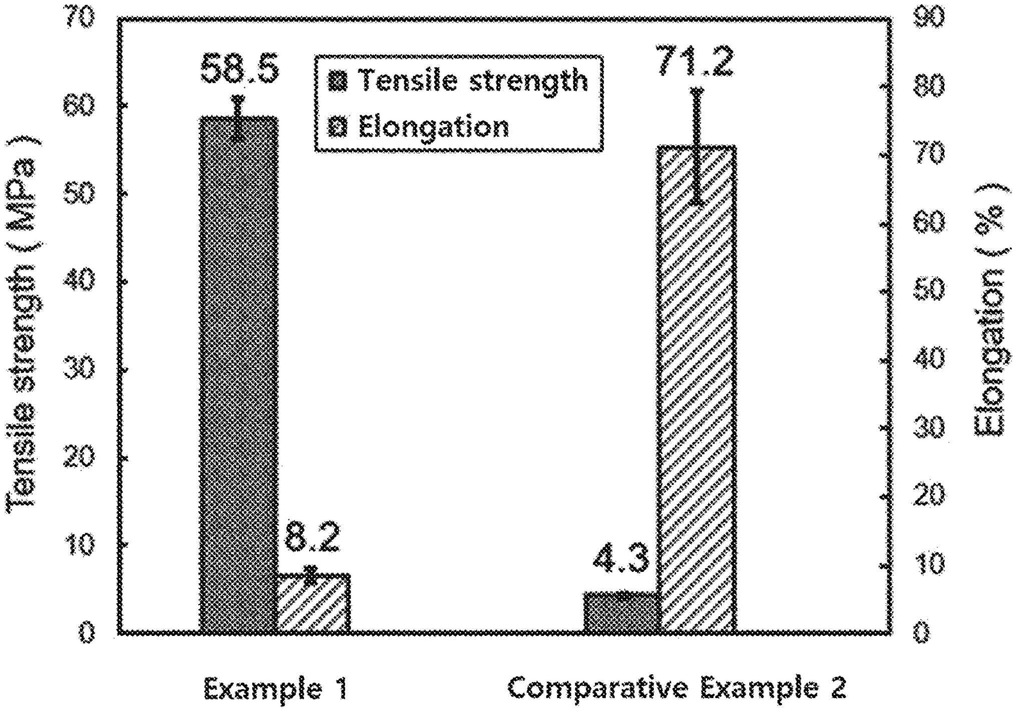
FIGS. 2A and 2B are graphs showing the tensile strength and elongation of the examples and comparative examples of the present invention.

More specifically, referring to FIG. 2A, it can be seen that the elongation of the porous polymer layer 37 including the pores 33 according to the present invention has a value close to about 900% compared to the elongation of the polymer layer 37 that does not include the pores 33. As such, the presence of pores may affect not only the elongation of the porous polymer layer 37, but also the elongation of the degradation control unit 30 including the porous polymer layer 37. In addition, referring to FIG. 2B, it can be seen that the porous polymer layer 37 has a different elongation according to the type of the biocompatible oil which is supported in the internal pores 33.

That is, by adjusting the presence of absence of the pores 33 of the above-described porous polymer layer 37 and the type of the biocompatible oil which is supported therein to be suitable for the use of the composite 100 for controlling the degradation of transient electronics according to the present invention, the degradation control unit 30 can control the elongation, and through this, the composite 100 for controlling the degradation of transient electronics is introduced into the body and is flexibly attached to the inside of the target body without damaging organs and the like such that it can perform the function for a predetermined period of time.

To this end, the degradation control unit 30 according to the present invention may exhibit an elongation of 60% or more by adjusting the types of the pores 33 and the biocompatible oil 35 described above. In this case, if the elongation of the degradation control unit 30 is less than 60%, it may be injected into the body to damage organs and the like, and there may be a problem in that the degradation time of the transient electronics 20 cannot be completely controlled due to deterioration in adhesion to the inside of the target living body.

Hereinafter, the method for controlling the degradation time of the transient electronics 20 through the degradation control unit 30 of the composite 100 for controlling the degradation according to the present invention will be described in detail.

The degradation time point of the transient electronics 20 may be affected by the surface window size, pore structure, pore shape and porosity that are related to the porous structure of the porous polymer layer 37. In addition, it may be affected by the thickness, density, shape, material and dissolution rate of the porous polymer layer 37 in the biological fluid. In addition, it may be affected by the viscosity and material of the biocompatible oil 35, the support amount which is supported in the porous polymer layer 37 and the reactivity and solubility with biological fluids. Therefore, the above factors may be used as factors for controlling the decomposition time point of the transient electronics 20 for the biological fluid.

For example, in the present invention, the degradation time of the transient electronics 20 can be controlled by adjusting the porosity of the porous polymer layer 37. That is, as the number of internal pores 33 of the porous polymer layer 37 increases, a greater amount of the biocompatible oil 35 is discharged for a shorter period of time, and since the biological fluid 40 can be introduced into the pores 33 inside the porous polymer layer 37, it is possible to rapidly promote the degradation of the transient electronics 20. Conversely, as the number of the internal pores 33 of the porous polymer layer 37 is smaller, the biocompatible oil 35 which is introduced into the internal pores 33 is discharged more slowly, and since the biological fluid 40 is also introduced slowly, it is possible to slowly control the degradation of the transient electronics 20.

To this end, the porous polymer layer 37 according to the present invention may have a porosity of 10 to 90%. In this case, if the porosity of the porous polymer layer 37 is less than 10%, since the amount of the biological fluid 40 that can be introduced into the pores 33 of the porous polymer layer 37 is extremely small, there may be a problem in that the degradation of the transient electronics 20 cannot be controlled. In addition, if the porosity of the porous polymer layer 37 is more than 90%, since the biocompatible oil 35 which is supported in the internal pores 33 of the porous polymer layer 37 is discharged too quickly, it may be difficult to control the degradation of the transient electronics 20.

Next, in the present invention, by adjusting the size of the window formed on a first surface which is connected to the internal pores 33 of the porous polymer layer 37 and in contact with the transient electronics 20 and a second surface which is opposite to the first surface in contact with the biological fluid, it is possible to control the degradation time of the transient electronics 20, or the degradation time of the transient electronics 20 can be controlled by adjusting the size of the pores 33 inside the porous polymer layer 37. That is, when the size of the internal pores 33 of the porous polymer layer 37 is large or the size of the second surface is large, a larger amount of the biocompatible oil 35 is discharged in a short period of time, and since the biological fluid 40 can be introduced into the internal pores 33 of the porous polymer layer 37, it is possible to rapidly promote the degradation of the transient electronics 20. Conversely, when the size of the internal pores 33 of the porous polymer layer 37 is small or the size of the first surface is small, the biocompatible oil 35 which is introduced into the internal pores 33 is discharged more slowly, and since the biological fluid 40 is also slowly introduced, it is possible to slowly control the degradation of the transient electronics.

To this end, the size of the internal pores 33 of the porous polymer layer 37 according to the present invention may be 10 nm to 200 nm. In this case, if the size of the internal pores 33 of the porous polymer layer 37 is less than 10 nm, since the amount of the biological fluid 40 that can be introduced into the internal pores 33 of the porous polymer layer 37 is very small, there may be a problem in that the degradation of the transient electronics 20 cannot be controlled. In addition, if the size of the internal pores 33 of the porous polymer layer 37 is more than 200 nm, the biocompatible oil 35 which is supported in the internal pores 33 of the porous polymer layer 37 is discharged too quickly, and similarly, there may be a problem in that the degradation of the transient electronics cannot be controlled. However, this is only one example of the present invention, and the above-described degradation time may be controlled to be faster or slower or vice versa according to the density, porosity, shape and the like, as well as the size of the above-described first surface, second surface or internal pores 33.

Figure 3A:
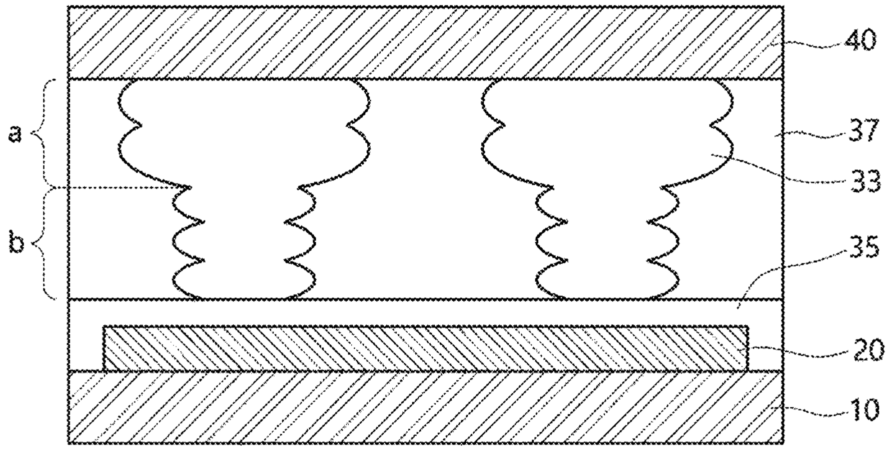
FIGS. 3A and 3B are cross-sectional diagrams of the composite for controlling the degradation of transient electronics according to an exemplary embodiment of the present invention.
Figure 3B:
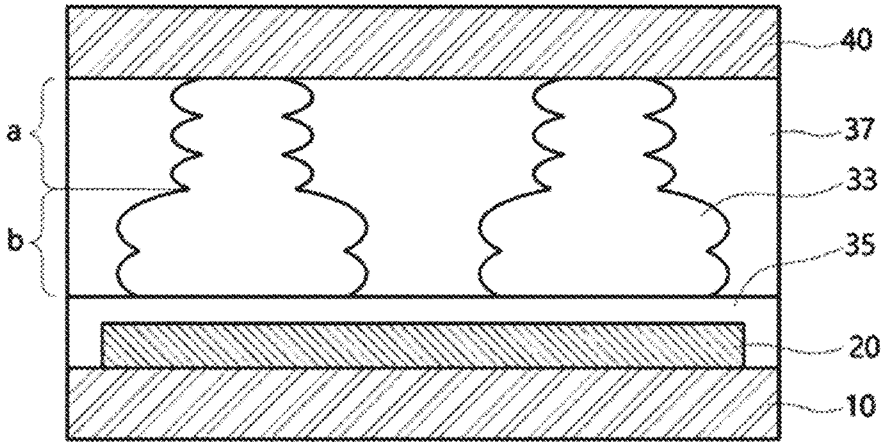
Figure 4:
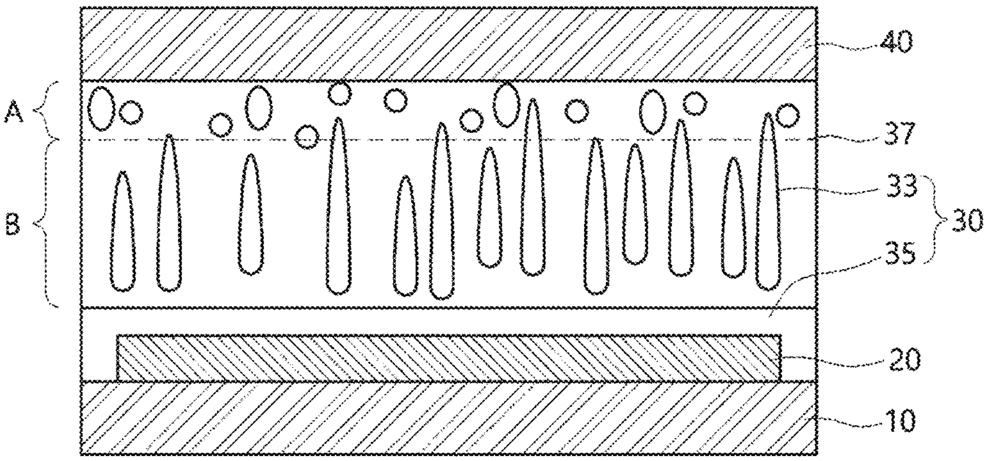
FIG. 4 is a cross-sectional diagram of the composite for controlling the degradation of transient electronics according to an exemplary embodiment of the present invention.

Next, in the present invention, the porous polymer layer 37 includes at least two or more internal pores 33 having different sizes, and it is possible to control the degradation time of the transient electronics 20 by adjusting their sizes differently. That is, as illustrated in FIG. 3A, when the size of internal pores formed on a first part (a) which is close to the first surface in contact with the biological fluid is larger than the size of internal pores formed on a second part (b) which is close to the second surface which is continuous with the first part (a) and is in contact with the transient electronics 20, a large amount of the biological fluid 40 is introduced into the internal pores (a) of the first part (a) such that the biocompatible oil 35 can be discharged more quickly through the internal pores (b), and as a result, the biological fluid 40 can rapidly promote the degradation of the transient electronics 20. Conversely, as illustrated in FIG. 3B, when the size of the internal pores (a) on a part in which the biological fluid is introduced is smaller than the size of the internal pores (b) through which the biocompatible oil 35 is discharged, that is, when the size of the second surface is smaller than the size of the first surface, a small amount of the biological fluid 40 is introduced into the internal pores (a) to allow the biocompatible oil 35 to be discharged more slowly through the internal pores (b), and as a result, the biological fluid can slowly control the degradation of the transient electronics 20.

Meanwhile, it may further include a flow path (not illustrated) which is connected between the window and the internal pores of the first surface or the second surface. The flow path may be a passage through which the biological fluid 40 or the biocompatible oil 35 passes.

Next, in the present invention, by adjusting the shape of the internal pores 33 of the porous polymer layer 37 differently, it is possible to control the degradation time of the transient electronics. According to an exemplary embodiment of the present invention, the internal pores 33 of the porous polymer layer 37 may be composed of a first part and a second part having different structures in the thickness direction of the porous polymer layer 37. That is, referring to FIG. 4, the internal pores 33 corresponding to the first part (A) may have an elliptical or circular shape with an aspect ratio close to 1. The internal pores 33 corresponding to the second part (B) may have a fingerlike shape with an aspect ratio of 5 or more, and through this, it may be more advantageous to achieve the objects of the present invention. However, since this is a preferred example of the present invention, the shape is not limited thereto, and it may be composed of internal pores 33 having the known conventional shape.

Next, in the present invention, by adjusting the amount of the biocompatible oil 33 which is supported in the internal pores 33 of the porous polymer layer 37, it is possible to control the degradation time of the transient electronics. That is, as the amount of the biocompatible oil 33 which is supported in the internal pores 33 of the porous polymer layer 37 is smaller, the biocompatible oil 35 is discharged in a short period of time, and since the biological fluid 40 can be introduced into the internal pores 33 of the porous polymer layer 37, it is possible to rapidly promote the degradation of the transient electronics. Conversely, as the amount of the biocompatible oil 35 which is supported in the internal pores 33 of the porous polymer layer 37 is large, the time for the biocompatible oil 35 introduced into the internal pores 33 to be discharged becomes longer, and since the biological fluid 40 is also slowly introduced, it is possible to slowly control the degradation of the transient electronics 20.

As such, the present invention can control the degradation time of the transient electronics 20 that the related art could not solve by adjusting the size, shape, density and average porosity of the internal pores 33 of the porous polymer layer 37 or the amount of biocompatible oil 35, and thus, according to a preferred exemplary embodiment of the present invention, the present invention provides a bio-insertable medical device including the above-described composite for controlling the degradation of transient electronics, which is a high-tech bio-insertable medical device that implements a function of diagnosis or treatment inside the living body and is absorbed into the living body through biodegradation.

Hereinafter, the present invention will be described in more detail through examples, but the following examples are not intended to limit the scope of the present invention, which should be construed to aid understanding of the present invention.

Example 1

(1) Preparation of Porous Polymer Layer

Figure 5A:
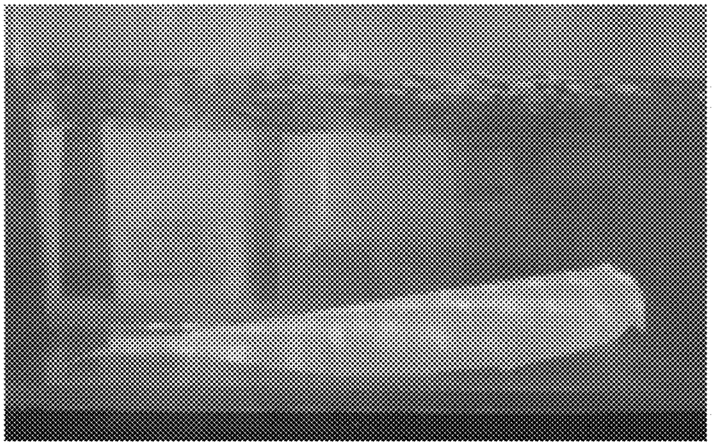
FIGS. 5A, 5B and 5C are photographs showing the composite for controlling the degradation of transient electronics according to an exemplary embodiment of the present invention.
Figure 5B:
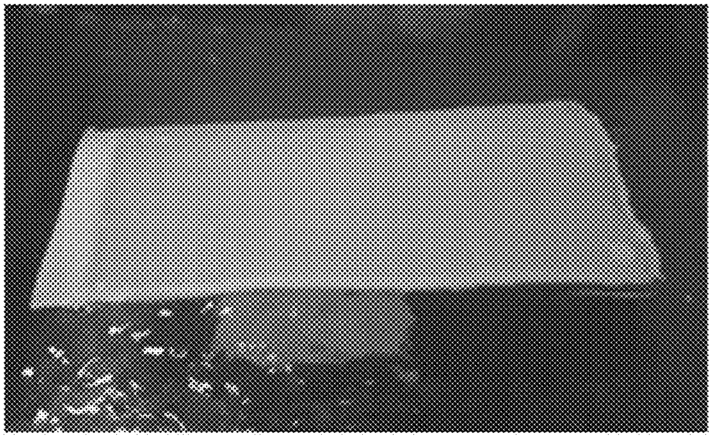
Figure 5C:
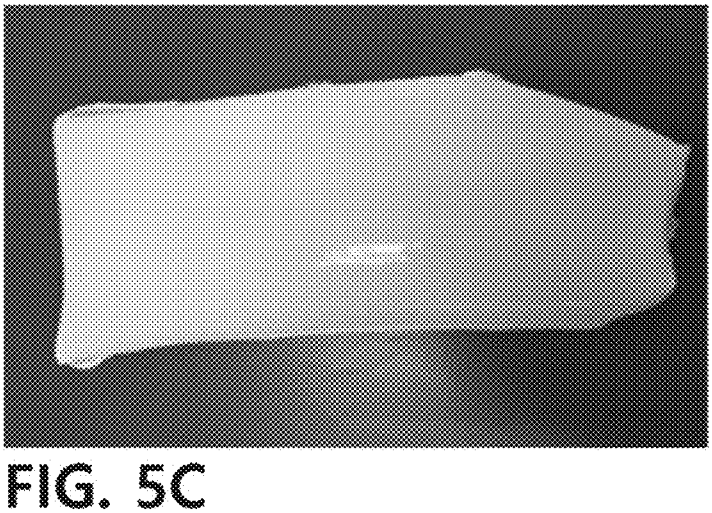

Specifically, porous PLA was fabricated by using PLA (Nature works, Mw~150,000) and N-methyl-2-pyrrolidone (NMP, Samchun Chemical). Afterwards, PLA was completely dissolved in NMP at 20 wt. % in NMP at 120° C. and stored in an oven at 70° C. Next, 4 mL of the PLA-dissolved solution was sprayed on a glass plate (30 cm*30 cm), and a thin liquid film was made with a uniform thickness (50 μm to 140 μm) by utilizing a doctor blade. Afterwards, the PLA liquid film and the glass plate on which the liquid film was placed were solidified by immersing in a solution containing distilled water as a non-solvent, and this was shown in FIG. 5A, and as shown in FIG. 5B, a porous polymer layer was prepared by vacuum drying the solidified porous PLA membrane in a desiccator at room temperature for 48 hours.

Figure 5D:
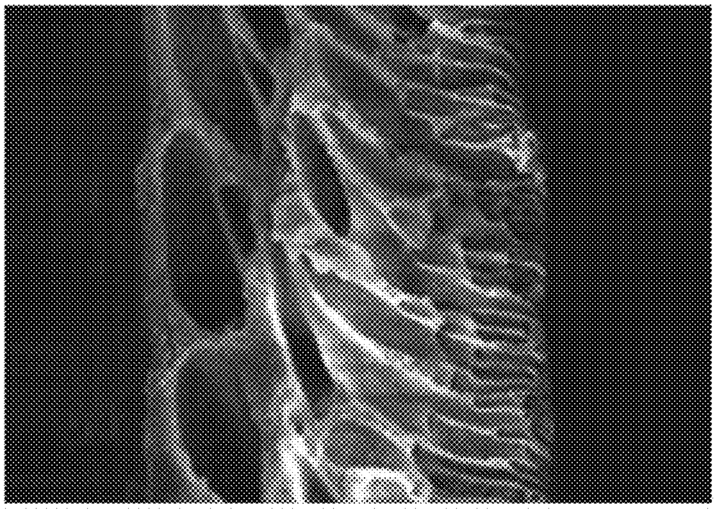
FIG. 5D is an SEM image of the composite for controlling the degradation of transient electronics according to an exemplary embodiment of the present invention.

By utilizing a scanning electron microscope (SEM, jeol jsm 6610), the fabricated PLA and pores were confirmed (FIG. 5D).

(2) Manufacture of Degradation Control Unit

By immersing the biodegradable polymer layer prepared in (1) above in silicone oil, which is a hydrophobic biocompatible oil, for 24 hours, the hydrophobic biocompatible oil was allowed to completely fill the internal pores of the biodegradable polymer layer as shown in FIG. 5D.

(3) Preparation of Composite for Controlling Degradation of Transient Electronics The degradation control unit manufactured in (2) above was formed by E-beam deposition on a support (platinum) having a thickness of 200 nm, and platinum, which is a water-soluble inorganic conductive element, was interposed between the degradation control unit and the support as transient electronics to prepare a composite for controlling the degradation of transient electronics.

Example 2

It was prepared in the same manner as in Example 1, except that the material of (2) the biodegradable polymer layer in Example 1 above was prepared by using polycaprolactone (PCL).

Examples 3 to 5

These were prepared in the same manner as in Example 1, except that (2) the biocompatible oil in Example 1 was changed as shown in Table 1 below.

Examples 6 and 7

These were prepared in the same manner as in Example 1, except that the viscosity of (2) the biocompatible oil in Example 1 above was changed as shown in Table 1 below.

Example 8

It was prepared in the same manner as in Example 1, except that (3) the transient electronics in Example 1 above were prepared by using molybdenum instead of platinum.

Examples 9 to 10

These were prepared in the same manner as in Example 1, except that the viscosity of (2) the biocompatible oil in Example 8 was changed as shown in Table 1 below.

Comparative Example 1

It was prepared in the same manner as in Example 1 above, except that the degradation control unit was manufactured by using (2) a polymer layer without pores.

Comparative Example 2

It was prepared in the same manner as in Example 1 above, except that the degradation control unit was manufactured by preparing (2) the porous polymer layer but not immersing in the biocompatible oil.

Comparative Example 3

It was prepared in the same manner as Example 1 above, except that the degradation control unit was manufactured by using a (2) polymer layer without pores and immersing in the biocompatible oil.

TABLE 1

| | Degradation Control Unit | | | | |
|---|---|---|---|---|---|
| | Biodegradable polymer | | | Transient Electronics | |
| | Presence of pores | Type | Oil | Viscosity (cst) | Type |
| Example 1 | ○ | PLA | Silicon oil | 50 | Pt |
| Example 2 | ○ | PCL | Silicon oil | 50 | Pt |
| Example 3 | ○ | PLA | Phosphate-buffered, Saline | 50 | Pt |
| Example 4 | ○ | PLA | KRYTOX | 50 | Pt |
| Example 5 | ○ | PLA | Canola oil | 50 | Pt |
| Example 6 | ○ | PLA | Silicon oil | 350 | Pt |
| Example 7 | ○ | PLA | Silicon oil | 1000 | Pt |
| Example 8 | ○ | PLA | Silicon oil | 50 | Mo |
| Example 9 | ○ | PLA | Silicon oil | 350 | Mo |
| Example 10 | ○ | PLA | Silicon oil | 1000 | Mo |
| Comparative Example 1 | x | PLA | No oil used | 50 | Pt |
| Comparative Example 2 | x | PLA | Silicon oil | 50 | Pt |
| Comparative Example 3 | ○ | PLA | No oil used | 50 | Pt |
| Comparative Example 4 | x | PLA | Silicon oil | 50 | Mo |

Experimental Example 1

After Example 1 and Comparative Example 2 were stored at 37° C. for 9 days, tensile strength and elongation were measured by using Instron, and the results are shown in FIG. 2A.

Referring to FIG. 2A, in the case of Example 1 including pores according to the present invention, it can be seen that the elongation had a value close to about 900% compared to the elongation of Comparative Example 2 without pores. Through this, it can be seen that the composite for controlling the degradation of transient electronics according to the present invention is implemented in the form of a porous polymer layer, and thus, it has excellent elongation and exhibits flexibility enough not to damage organs and the like such that it has sufficient stability and biocompatibility.

Experimental Example 2

Figure 2B:
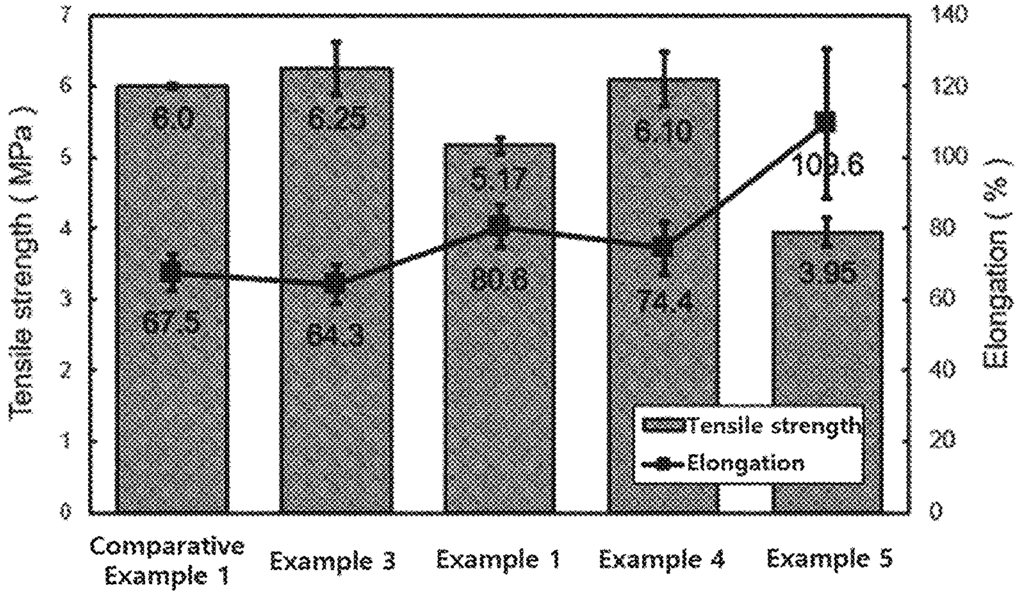

After Examples 1, 3 to 5 and Comparative Example 3 were stored at 37° C. for 9 days, tensile strength and elongation were measured by using Instron, and the results are shown in FIG. 2B.

Referring to FIG. 2B, it can be seen that the elongation is different depending on the type of the biocompatible oil supported on the porous polymer layer. Through this, it can be seen that the composite for controlling the degradation of transient electronics according to the present invention can control the elongation by using a different oil to be suitable for a desired use (attachment site, etc.).

Experimental Example 3

Figure 6:
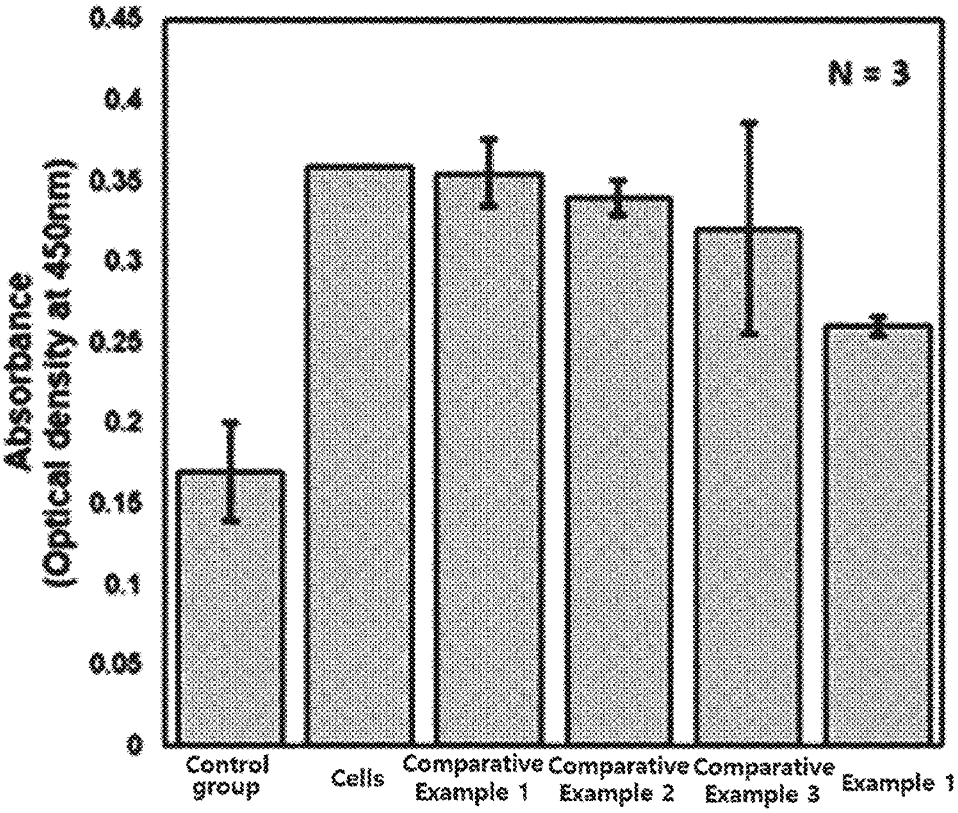
FIG. 6 is a graph showing the cytotoxicity experiment results of transient electronics according to the examples and comparative examples of the present invention.

Example 1 and Comparative Examples 1 to 3 were placed in a 24-well plate of IH3T3 (ACTC cell line, 5 passages) at 7,000 cells/well for each well, and these were placed in 700 μL of DMEM medium containing 10% FBS and cultured for 24 hours in a 5% CO2 incubator, 37%. Afterwards, 70 μL of cck-8 solution (Dojindo, Japan) was added to measure cytotoxicity three times, and the results are shown in FIG. 6.

Experimental Example 4

Examples 1, 6 to 10 and Comparative Examples 2 and 4 were immersed in an aqueous solution (0.1M, PBS) to measure the degradation time over time, and the results are shown in FIGS. 7 to 10.

Figure 7:
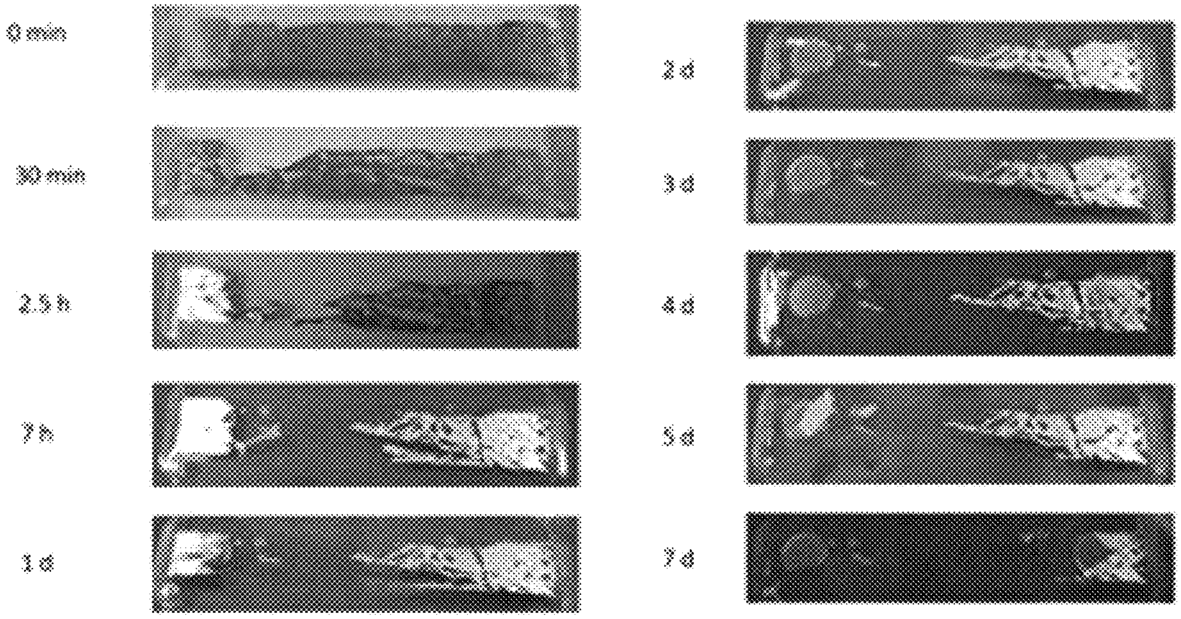
FIGS. 7 to 10 are photographs showing the degree of degradation according to the passage of time of the transient electronics according to the examples and comparative examples of the present invention.

FIG. 7 is a photograph showing the decomposition of Comparative Example 2 (platinum) over time. That is, in the case of Comparative Example 2, since it was not prepared with a porous polymer layer, it can be seen that the degradation time could not be controlled, and it gradually melted over time.

Figure 8:
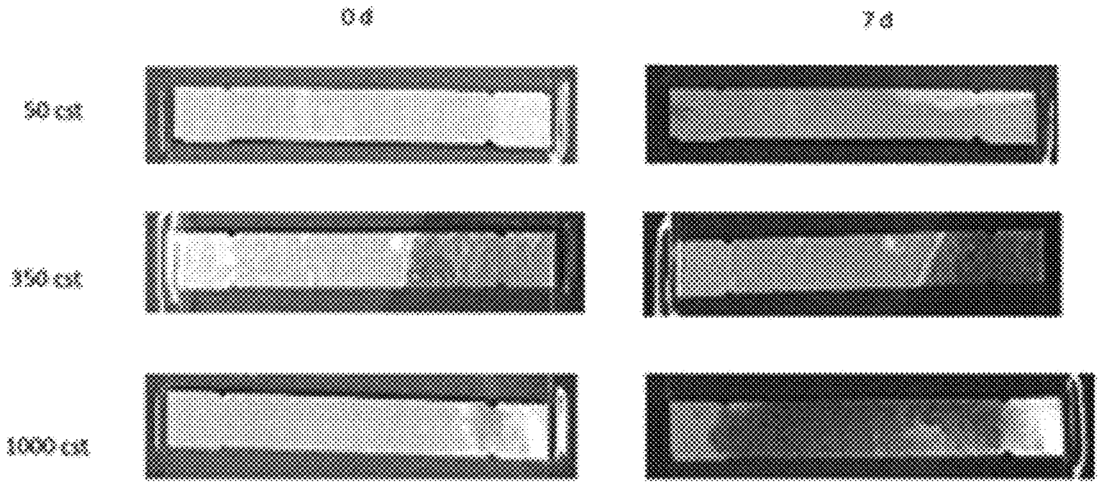

In contrast, FIG. 8 is a photograph showing the results of Examples 1, 6 and 7 according to the present invention. That is, when these were prepared with a porous polymer layer regardless of the viscosity of the oil used, these were not degraded even after 7 days, and through this, it can be seen that the degradation time can be controlled only when it is implemented with the porous polymer layer according to the present invention.

Figure 9:
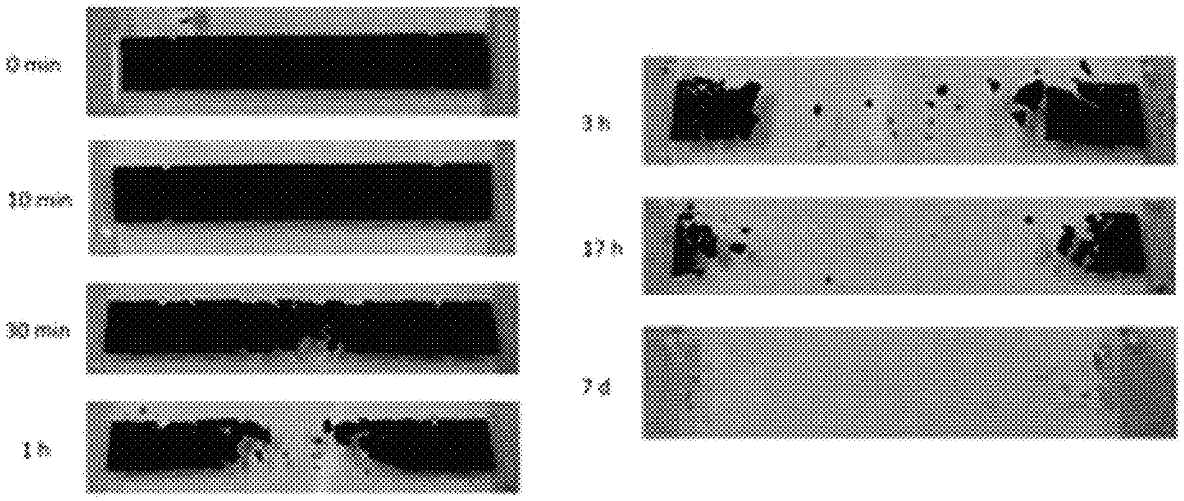

FIG. 9 is a photograph showing the decomposition of Comparative Example 4 (molybdenum) over time. That is, in the case of Comparative Example 4, since it was not prepared with a porous polymer layer, it can be seen that the degradation time could not be controlled and gradually melted with time.

Figure 10:
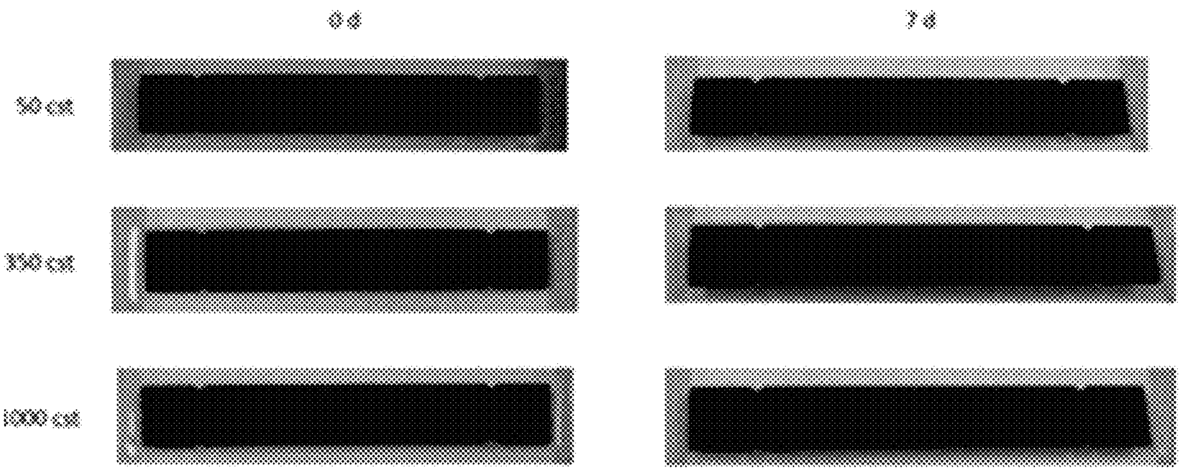

In contrast, FIG. 10 is a photograph showing the results of Examples 8 to 10 according to the present invention. That is, when these were prepared with a porous polymer layer regardless of the viscosity of the oil used, these were not degraded even after 7 days, and through this, it can be seen that the degradation time can be controlled only when it is implemented with the porous polymer layer according to the present invention.

The invention claimed is:

1. A composite configured to control degradation of transient electronics, which is a composite configured to control degradation of transient electronics that are degraded by a biological fluid at a desired degradation time point, the composite comprising:

a support;

transient electronics that are formed on the support; and a degradation control unit configured to control the degradation time point of the transient electronics by sealing the transient electronics from a biological fluid with a porous polymer layer in which biocompatible oil is supported in internal pores, wherein the transient electronics comprise at least one of a water-soluble conductive transient organic material or a water-soluble conductive transient inorganic material.

2. The composite of claim 1, wherein as time elapses after being in contact with the biological fluid, the biocompatible oil which is supported on the porous polymer layer of the composite flows out toward the biological fluid, and as a result, the biological fluid flowing into empty pores of the porous polymer layer eventually comes into contact with the transient electronics to degrade the transient electronics.

3. The composite of claim 1, wherein the support and the porous polymer layer comprise at least one selected from the group consisting of polycaprolactone (PCL), polydioxanone (PDO), poly(L-lactide) (PLLA), poly(DL-lactide-co-glycolide) (PLGA), polyethylene oxide (PEO), polylactic acid (PLA) and polyvinyl alcohol (PVA), and wherein the porous polymer layer is formed of a polymer which is soluble in the biological fluid in order to control the degradation time point of the transient electronics together with the biocompatible oil.

4. The composite of claim 1, wherein the transient electronics have a thickness of 10 to 1,000 nm.

5. The composite of claim 1, wherein the degradation control unit has an elongation of 60% or more.

6. The composite of claim 1, wherein the porous polymer layer comprises internal pores having different sizes.

7. The composite of claim 1, wherein the porosity of the porous polymer layer is 10 to 90%.

8. The composite of claim 1, wherein the porous polymer layer is composed of a first part and a second part that face a first surface on the first surface which is in contact with transient electronics and have different pore structures in the direction of a second surface which is in contact with the biological fluid.

9. The composite of claim 8, wherein at least one of the first part and the second part has a fingerlike shape.

10. The composite of claim 8, wherein the window diameter of a surface on the side of the first surface and the window diameter of a surface on the side of the second surface are different from each other.

11. The composite of claim 1, wherein the biocompatible oil is any one or more hydrophobic biocompatible oils selected from the group consisting of fluorine-based oil, silicone-based oil, mineral oil and vegetable oil.

* * * * *